United States Patent
Cheng et al.

(10) Patent No.: US 8,536,116 B2
(45) Date of Patent: Sep. 17, 2013

(54) ANTAGONISTS FOR DISEASES INDUCED BY CELLS WITH HIGH-AFFINITY ELR-CXC CHEMOKINE RECEPTOR PROTEINS

(75) Inventors: Jya-Wei Cheng, Hsinchu (TW); Kuo-Chun Huang, Hsinchu (TW); Hsi-Tsung Cheng, Hsinchu (TW); Hui-Yuan Yu, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 18 days.

(21) Appl. No.: 13/494,587

(22) Filed: Jun. 12, 2012

(65) Prior Publication Data
US 2013/0109614 A1  May 2, 2013

(30) Foreign Application Priority Data

Oct. 26, 2011  (TW) .............................. 100138960 A (51) Int. Cl.
*A61K 38/00* (2006.01)

(52) U.S. Cl.
USPC ........................................................ 514/1.1

(58) Field of Classification Search
None
See application file for complete search history.

*Primary Examiner* — Marcela M Cordero Garcia
*Assistant Examiner* — Kaipeen Yang
(74) *Attorney, Agent, or Firm* — Muncy, Geissler, Olds & Lowe (57) ABSTRACT

Enclosed is an antagonist, which includes a peptide chain represented by an amino acid sequence. The amino acid sequence has a short sequence, C-X1X2X3X4X5-N, which is situated before and neighbored to the third cysteine (Cys, C) of the N-terminus, wherein X1 is an amino acid with aromatic ring, hydrophobic property or long chain, and X2, X3, X4 and X5 are glutamine (G), serine (S), alanine (A) and proline (P) respectively. In one embodiment, X1 is phenylalanine (F). The present antagonists can be used to inhibit or treat with the diseases caused by the activated cells expressing CXCR1 and/or CXCR2 receptor, for example, the acute or chronic inflammatory reaction induced with polymorphonuclear neutrophils (PMNs) expressing CXCR1 and/or CXCR2 receptor, and angiogenesis accompanied by tumor growth inhibition.

11 Claims, 7 Drawing Sheets

SEQUENCE LISTING

<160> NUMBER OF SEQ ID NOS: 19

<210> SEQ ID NO 1
<211> LENGTH: 72
<212> TYPE: PRT
<213> ORGANISM: Artificial Sequence
<220> FEATURE:
<223> OTHER INFORMATION: Artificial ELR-CXC chemokine

<400> SEQUENCE: 1

Gly Ser Lys Glu Leu Arg Cys Gln Cys Ile Arg Thr Tyr Ser Lys Pro
1               5                   10                  15

Phe His Pro Lys Phe Ile Lys Glu Leu Arg Val Ile Glu Ser Pro Pro
                20                  25                  30

His Cys Ala Asn Thr Glu Ile Ile Val Lys Leu Ser Asp Gly Arg Glu
            35                  40                  45

Leu Cys Leu Asp Pro Lys Glu Asn Trp Val Gln Arg Val Val Glu Lys
        50                  55                  60

Phe Leu Lys Arg Ala Glu Asn Ser
65                  70

<210> SEQ ID NO 2
<211> LENGTH: 72
<212> TYPE: PRT
<213> ORGANISM: Homo sapiens

<400> SEQUENCE: 2

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
                20                  25                  30

His Cys Ala Asn Thr Glu Ile Ile Val Lys Leu Ser Asp Gly Arg Glu
            35                  40                  45

Leu Cys Leu Asp Pro Lys Glu Asn Trp Val Gln Arg Val Val Glu Lys
        50                  55                  60

Phe Leu Lys Arg Ala Glu Asn Ser
65                  70

<210> SEQ ID NO 3
<211> LENGTH: 74
<212> TYPE: PRT
<213> ORGANISM: Homo sapiens

<400> SEQUENCE: 3

Gly Ala Ser Val Ala Thr Glu Leu Arg Cys Gln Cys Leu Gln Thr Leu
1               5                   10                  15

Gln Gly Ile His Pro Lys Asn Ile Gln Ser Val Asn Val Lys Ser Pro
                20                  25                  30

Gly Pro His Cys Ala Gln Thr Glu Val Ile Ala Thr Leu Lys Asn Gly
            35                  40                  45

Arg Lys Ala Cys Leu Asn Pro Ala Ser Pro Ile Val Lys Lys Ile Ile
        50                  55                  60

Glu Lys Met Leu Asn Ser Asp Lys Ser Asn
65                  70

<210> SEQ ID NO 4
<211> LENGTH: 74
<212> TYPE: PRT
<213> ORGANISM: Homo sapiens

<400> SEQUENCE: 4

Gly Ala Pro Leu Ala Thr Glu Leu Arg Cys Gln Cys Leu Gln Thr Leu
1               5                   10                  15

Gln Gly Ile His Leu Lys Asn Ile Gln Ser Val Lys Val Lys Ser Pro
                20                  25                  30

Gly Pro His Cys Ala Gln Thr Glu Val Ile Ala Thr Leu Lys Asn Gly
            35                  40                  45

Gln Lys Ala Cys Leu Asn Pro Ala Ser Pro Met Val Lys Lys Ile Ile
        50                  55                  60

Glu Lys Met Leu Lys Asn Gly Lys Ser Asn
65                  70

<210> SEQ ID NO 5
<211> LENGTH: 74
<212> TYPE: PRT
<213> ORGANISM: Homo sapiens

<400> SEQUENCE: 5

Gly Ala Ser Val Val Thr Glu Leu Arg Cys Gln Cys Leu Gln Thr Leu
1               5                   10                  15

Gln Gly Ile His Leu Lys Asn Ile Gln Ser Val Asn Val Arg Ser Pro
                20                  25                  30

Gly Pro His Cys Ala Gln Thr Glu Val Ile Ala Thr Leu Lys Asn Gly
            35                  40                  45

Lys Lys Ala Cys Leu Asn Pro Ala Ser Pro Met Val Gln Lys Ile Ile
        50                  55                  60

Glu Lys Ile Leu Asn Lys Gly Ser Thr Asn
65                  70

<210> SEQ ID NO 6
<211> LENGTH: 73
<212> TYPE: PRT
<213> ORGANISM: Homo sapiens

<400> SEQUENCE: 6

Ala Val Leu Arg Glu Leu Arg Cys Val Cys Leu Gln Thr Thr Gln Gly
1               5                   10                  15

Val His Pro Lys Met Ile Ser Asn Leu Gln Val Phe Ala Ile Gly Pro
                20                  25                  30

Gln Cys Ser Lys Val Glu Val Val Ala Ser Leu Lys Asn Gly Lys Glu
            35                  40                  45

Ile Cys Leu Asp Pro Glu Ala Pro Phe Leu Lys Lys Val Ile Gln Lys
        50                  55                  60

Ile Leu Asp Gly Gly Asn Lys Glu Asn
65                  70

<210> SEQ ID NO 7
<211> LENGTH: 74
<212> TYPE: PRT
<213> ORGANISM: Homo sapiens

<400> SEQUENCE: 7

Ser Ala Val Leu Thr Glu Leu Arg Cys Thr Cys Leu Arg Val Thr Leu
1               5                   10                  15

Arg Val Asn Pro Lys Thr Ile Gly Lys Leu Gln Val Phe Pro Ala Gly
                20                  25                  30

Pro Gln Cys Ser Lys Val Glu Val Ala Ser Leu Lys Asn Gly Lys
            35                  40                  45

```
Gln Val Cys Leu Asp Pro Glu Ala Pro Phe Leu Lys Lys Val Ile Gln
    50                  55                  60

Lys Ile Leu Asp Ser Gly Asn Lys Lys Asn
65                  70

<210> SEQ ID NO 8
<211> LENGTH: 74
<212> TYPE: PRT
<213> ORGANISM: Homo sapiens

<400> SEQUENCE: 8

Ser Asp Leu Tyr Ala Glu Leu Arg Cys Met Cys Ile Lys Thr Thr Ser
1               5                   10                  15

Gly Ile His Pro Lys Asn Ile Gln Ser Leu Glu Val Ile Gly Lys Gly
                20                  25                  30

Thr His Cys Asn Gln Val Glu Val Ile Ala Thr Leu Lys Asp Gly Arg
            35                  40                  45

Lys Ile Cys Leu Asp Pro Asp Ala Pro Arg Ile Lys Lys Ile Val Gln
        50                  55                  60

Lys Lys Leu Ala Gly Asp Glu Ser Ala Asp
65                  70

<210> SEQ ID NO 9
<211> LENGTH: 73
<212> TYPE: PRT
<213> ORGANISM: Artificial Sequence
<220> FEATURE:
<223> OTHER INFORMATION: Artificial ELR-CXC chemokine

<400> SEQUENCE: 9

Ser Ala Lys Glu Leu Arg Cys Gln Ala Cys Ile Arg Thr Tyr Ser Lys
1               5                   10                  15

Pro Phe His Pro Lys Phe Ile Lys Glu Leu Arg Val Ile Glu Ser Gly
                20                  25                  30

Pro His Cys Ala Asn Thr Glu Ile Ile Val Lys Leu Ser Asp Gly Arg
            35                  40                  45

Glu Leu Cys Leu Asp Pro Lys Glu Asn Trp Val Gln Arg Val Val Glu
        50                  55                  60

Lys Phe Leu Lys Arg Ala Glu Asn Ser
65                  70

<210> SEQ ID NO 10
<211> LENGTH: 70
<212> TYPE: PRT
<213> ORGANISM: Artificial Sequence
<220> FEATURE:
<223> OTHER INFORMATION: Modified ELR-CXC Chemokine

<400> SEQUENCE: 10

Val Thr Glu Leu Arg Cys Gln Cys Leu Gln Thr Leu Gln Gly Ile His
1               5                   10                  15

Pro Lys Asn Ile Gln Ser Val Asn Val Lys Pro Ala Ser Gln Phe Cys
                20                  25                  30

Ala Glu Thr Glu Val Ile Ala Thr Leu Lys Asn Gly Gln Lys Ala Cys
            35                  40                  45

Leu Asn Pro Ala Ser Pro Met Val Gln Lys Ile Ile Lys Lys Met Leu
        50                  55                  60

Asn Cys Asp Lys Ser Asn
65                  70
```

-continued

```
<210> SEQ ID NO 11
<211> LENGTH: 107
<212> TYPE: PRT
<213> ORGANISM: Artificial Sequence
<220> FEATURE:
<223> OTHER INFORMATION: Modified ELR-CXC Chemokine

<400> SEQUENCE: 11

Met Ala Arg Ala Thr Leu Ser Ala Ala Pro Ser Asn Pro Arg Leu Leu
1 5 10 15

Arg Val Ala Leu Leu Leu Leu Leu Leu Val Ala Ala Ser Arg Arg Ala
20 25 30

Ala Gly Ala Pro Leu Ala Thr Glu Leu Arg Cys Gln Cys Leu Gln Thr
35 40 45

Leu Gln Gly Ile His Leu Lys Asn Ile Gln Ser Val Lys Val Lys Pro
50 55 60

Ala Ser Gln Phe Cys Ala Gln Thr Glu Val Ile Ala Thr Leu Lys Asn
65 70 75 80

Gly Gln Lys Ala Cys Leu Asn Pro Ala Ser Pro Met Val Lys Lys Ile
85 90 95

Ile Glu Lys Met Leu Lys Asn Gly Lys Ser Asn
100 105

<210> SEQ ID NO 12
<211> LENGTH: 73
<212> TYPE: PRT
<213> ORGANISM: Artificial Sequence
<220> FEATURE:
<223> OTHER INFORMATION: Modified ELR-CXC Chemokine

<400> SEQUENCE: 12

Ala Ser Val Val Thr Glu Leu Arg Cys Gln Cys Leu Gln Thr Leu Gln
1 5 10 15

Gly Ile His Leu Lys Asn Ile Gln Ser Val Asn Val Arg Pro Ala Ser
20 25 30

Gln Phe Cys Ala Gln Thr Glu Val Ile Ala Thr Leu Lys Asn Gly Lys
35 40 45

Lys Ala Cys Leu Asn Pro Ala Ser Pro Met Val Gln Lys Ile Ile Glu
50 55 60

Lys Ile Leu Asn Lys Gly Ser Thr Asn
65 70

<210> SEQ ID NO 13
<211> LENGTH: 91
<212> TYPE: PRT
<213> ORGANISM: Artificial Sequence
<220> FEATURE:
<223> OTHER INFORMATION: Modified ELR-CXC Chemokine

<400> SEQUENCE: 13

Ala Pro Ser Ser Val Ile Ala Ala Thr Glu Leu Arg Cys Val Cys Leu
1 5 10 15

Thr Val Thr Pro Lys Ile Asn Pro Lys Leu Ile Ala Asn Leu Glu Val
20 25 30

Ile Pro Ala Ser Gln Phe Cys Pro Thr Val Glu Val Ile Ala Lys Leu
35 40 45

Lys Asn Gln Lys Glu Val Cys Leu Asp Pro Glu Ala Pro Val Ile Lys
50 55 60

Lys Ile Ile Gln Lys Ile Leu Gly Ser Asp Lys Lys Lys Ala Lys Arg
65 70 75 80
```

```
Asn Ala Leu Ala Val Glu Arg Thr Ala Ser Val
             85                  90

<210> SEQ ID NO 14
<211> LENGTH: 74
<212> TYPE: PRT
<213> ORGANISM: Artificial Sequence
<220> FEATURE:
<223> OTHER INFORMATION: Modified ELR-CXC Chemikine

<400> SEQUENCE: 14

Ser Ala Val Leu Thr Glu Leu Arg Cys Thr Cys Leu Arg Val Thr Leu
1               5                   10                  15

Arg Val Asn Pro Lys Thr Ile Gly Lys Leu Gln Val Phe Pro Ala Ser
            20                  25                  30

Gln Phe Cys Ser Lys Val Glu Val Ala Ser Leu Lys Asn Gly Lys
        35                  40                  45

Gln Val Cys Leu Asp Pro Glu Ala Pro Phe Leu Lys Lys Val Ile Gln
    50                  55                  60

Lys Ile Leu Asp Ser Gly Asn Lys Lys Asn
65                  70

<210> SEQ ID NO 15
<211> LENGTH: 78
<212> TYPE: PRT
<213> ORGANISM: Artificial Sequence
<220> FEATURE:
<223> OTHER INFORMATION: Modified ELR-CXC Chemikine

<400> SEQUENCE: 15

Glu Ser Leu Asp Ser Asp Leu Tyr Ala Glu Leu Arg Cys Met Cys Ile
1               5                   10                  15

Lys Thr Thr Ser Gly Ile His Pro Lys Asn Ile Gln Ser Leu Glu Val
            20                  25                  30

Ile Pro Ala Ser Gln Phe Cys Asn Gln Val Glu Val Ile Ala Thr Leu
        35                  40                  45

Lys Asp Gly Arg Lys Ile Cys Leu Asp Pro Asp Ala Pro Arg Ile Lys
    50                  55                  60

Lys Ile Val Gln Lys Lys Leu Ala Gly Asp Glu Ser Ala Asp
65                  70                  75

<210> SEQ ID NO 16
<211> LENGTH: 78
<212> TYPE: PRT
<213> ORGANISM: Artificial Sequence
<220> FEATURE:
<223> OTHER INFORMATION: Modified ELR-CXC Chemokine

<400> SEQUENCE: 16

Glu Ser Leu Asp Ser Asp Leu Tyr Ala Glu Leu Arg Cys Met Cys Ile
1               5                   10                  15

Lys Thr Thr Ser Gly Ile His Pro Lys Asn Ile Gln Ser Leu Glu Val
            20                  25                  30

Ile Pro Ala Ser Gln Phe Cys Asn Gln Val Glu Val Ile Ala Thr Leu
        35                  40                  45

Lys Asp Gly Arg Lys Ile Cys Leu Asp Pro Asp Ala Pro Arg Ile Lys
    50                  55                  60

Lys Ile Val Gln Lys Lys Leu Ala Gly Asp Glu Ser Ala Asp
65                  70                  75
```

-continued

```
<210> SEQ ID NO 17
<211> LENGTH: 72
<212> TYPE: PRT
<213> ORGANISM: Artificial Sequence
<220> FEATURE:
<223> OTHER INFORMATION: Modified ELR-CXC Chemokine

<400> SEQUENCE: 17

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Pro Ala Ser Gln
                20                  25                  30

Phe Cys Ala Asn Thr Glu Ile Ile Val Lys Leu Ser Asp Gly Arg Glu
            35                  40                  45

Leu Cys Leu Asp Pro Lys Glu Asn Trp Val Gln Arg Val Val Glu Lys
        50                  55                  60

Phe Leu Lys Arg Ala Glu Asn Ser
65                  70

<210> SEQ ID NO 18
<211> LENGTH: 71
<212> TYPE: PRT
<213> ORGANISM: Artificial Sequence
<220> FEATURE:
<223> OTHER INFORMATION: Modified ELR-CXC Chemokine

<400> SEQUENCE: 18

Ser Ala Lys Glu Leu Arg Cys Cys Ile Arg Thr Tyr Ser Lys Pro Phe
1               5                   10                  15

His Pro Lys Phe Ile Lys Glu Leu Arg Val Ile Pro Ala Ser Gln Phe
                20                  25                  30

Cys Ala Asn Thr Glu Ile Ile Val Lys Leu Ser Asp Gly Arg Glu Leu
            35                  40                  45

Cys Leu Asp Pro Lys Glu Asn Trp Val Gln Arg Val Val Glu Lys Phe
        50                  55                  60

Leu Lys Arg Ala Glu Asn Ser
65                  70

<210> SEQ ID NO 19
<211> LENGTH: 72
<212> TYPE: PRT
<213> ORGANISM: Artificial Sequence
<220> FEATURE:
<223> OTHER INFORMATION: Modified ELR-CXC Chemokine

<400> SEQUENCE: 19

Gly Ser Lys Glu Leu Arg Cys Gln Cys Ile Arg Thr Tyr Ser Lys Pro
1               5                   10                  15

Phe His Pro Lys Phe Ile Lys Glu Leu Arg Val Ile Pro Ala Ser Gln
                20                  25                  30

Phe Cys Ala Asn Thr Glu Ile Ile Val Lys Leu Ser Asp Gly Arg Glu
            35                  40                  45

Leu Cys Leu Asp Pro Lys Glu Asn Trp Val Gln Arg Val Val Glu Lys
        50                  55                  60

Phe Leu Lys Arg Ala Glu Asn Ser
65                  70
```

ANTAGONISTS FOR DISEASES INDUCED BY CELLS WITH HIGH-AFFINITY ELR-CXC CHEMOKINE RECEPTOR PROTEINS

CROSS-REFERENCE TO RELATED APPLICATIONS

This Non-provisional application claims priority under 35 U.S.C. §119(a) on Patent Application No. 100138960 filed in Taiwan, Republic of China Oct. 26, 2011, the entire contents of which are hereby incorporated by reference.

FIELD OF THE INVENTION

This invention relates to a modified chemokine peptide capable of being a therapeutic antagonist. In particular, this invention relates to a therapeutic antagonist for diseases induced by cells with high-affinity ELR-CXC chemokine receptor proteins.

BACKGROUND OF THE INVENTION

Chemokine usually has three β-sheets in its structure, and has an α-helix at C terminal and 4 conserved cysteines at N-terminus. In accordance with the sequence containing the first two cysteines at N-terminus, chemokine is divided as four groups, CXC, CC, C and CX3C, and CC and CXC chemokines are the major ones. Reaction happens after chemokine on the cell conjugated with chemokine receptor. Chemokine receptor includes seven transmembrane G protein binding receptors, which respectively are nominated as CXCR, CCR, CXR and $CX_3CR$ according to the types of ligands on the binding target. Chemokine receptors are further arranged according to the number, such as CXCR1, CXCR2, CXCR4 and so on. However, not only one chemokine receptor is represented on the target cells, the binding target of the infiltrated inflammation cells is not specifically to one chemokine receptor, and then some chemokine receptors of different cells must be expressed under certain stimulation and induction.

For instance, ELR-CXC chemokine with glutamate (E)-leucine (L)-Arginine (R) characteristic sequence (ELR characteristic sequence) is referred to a protein having the amino acid sequence of ELR-CXC characteristic at N-terminus, and X would be the amino acid having polarity and w/o charge, or X is absent. ELR-CXC chemokine can regulate the expression of carcinogen, IL-8 and neutrophil-activating protein-2 (NAP-2). Its receptors are CXCR1 and CXCR2, and its major target cells are neutrophils, ELR-CXC chemokine can promote the accumulation and activation of neutrophils. Thus, this type of ELR-CXC chemokine plays an important role in the generation of the board-ranged acute and chronic inflammation diseases. These inflammations include psoriasis and rheumatoid arthritis.

Additionally, ELR-CXC chemokine further is associated with angiogenesis accompanied upon tumor development, and its inductive mechanism is the activation generated by conjugating this type of chemokine, especially referring to IL-8, with CXCR1 and CXCR2 on the endothelial cells (ECs). At present, it is proved that many different types of tumors are able to reproduce ELR-CXC chemokines, and the tumors expressing these types of chemokines are deemed to be associated with the tumor development after poor prognosis.

Anti-conjugation of CXCR1 or CXCR2 with ELR-CXC chemokine is a practicable strategy, so that the abnormal signal transmission induced by the activation of CXCR1 or/and CXCR2 receptor is inhibited, so that the associated diseases resulted from the activation of cells with two types of receptors are treated. Accordingly, scientists are endeavoring in finding and preparing receptor protein analogs for inhibiting CXC chemokines.

It is therefore attempted by the applicant to deal with the above situation encountered in the prior art.

SUMMARY OF THE INVENTION

This invention is referred to a modified chemokine peptide, which is an analog protein for inhibiting CXCR1 or/and CXCR2 receptor proteins (or named as ELR-CXC chemokine or ELR-CXC). Replacement, addition or deletion is made by modification on the specific amino acid position, so that the characteristic sequence of CXCL8 (ELR-CXC) is conjugated with the 30s-loop region of CXCL10. Therefore, the modified chemokine peptide has high affinity on CXCR1 and CXCR2, and simultaneously has a structure similar to the residue orientation of 30 loop position of CXCL10, so that inhibition of the signal transmission function of these receptor proteins (such as CXCL1, CXCL2, CXCL3, CXCL5, CXCL6, CXCL7 or CXCL8) on its receptors is achieved. For example, the receptor proteins of these specific receptors binding to CXCR1 or/and CXCR2 receptors can be blocked, or the abnormal signal transmission induced by high-affinity receptor protein binding to CXCR1 or/and CXCR2 receptors is blocked, interfered or reduced, to further treat the associated diseases resulted from the psychological functions. More detailed, the invention provides a receptor protein analog of CXCR1 or CXCR2 transmembrane receptor protein, also nominated as ELR-CXC chemokine analog, which is a modified chemokine peptide. Modification is achieved via the method of mutation, addition, deletion or artificial synthesis, so that N-terminus of the amino acid sequence has a glutamate (E)-leucine (L)-Arginine (R) characteristic sequence and a modified sequence. The modified sequence is located in the upstream of the third cysteine (Cys3) counted from N-terminus, and there is a sequence represented as $X_5X_4X_3X_2X_1$-Cys3 which is labeled from the third cysteine (Cys3) to N-terminus, wherein $X_1$ can be any amino acid, $X_2$ is glutamine (Q), $X_3$ is serine (S), $X_4$ is alanine (A) and $X_5$ is proline (P). This modified chemokine peptide can generate a structure which has a part of residues with an extroversion loop, has high affinity on CXCR1 or/and CXCR2 receptor protein, can be used to treat diseases resulted from the abnormal signal transmission of cells which have two types of receptors induced by the activation of ELR-CXC chemokine, and is used as a therapeutic antagonist.

In addition to a glutamate (E)-leucine (L)-Arginine (R) characteristic sequence at N-terminus, this modified chemokine peptide (ELR-CXC chemokine analog) has a specific motif of ELR-$CX_nC$, wherein X can be an amino acid having polarity and with or without charge or X is absent, n is referred to the number of acid between the first two cysteines (C) counted from N-terminus, and n usually can 0 to 2.

In addition to the above ELR characteristic sequence, modification is further made on the specific position of amino acid, so that a modified sequence is taken. The modified sequence makes the structure of this invention has an extroversion loop structure to have high affinity on CXCR1 or CXCR2.

This invention also provide a therapeutic antagonist, including a peptide chain having an amino acid sequence represented as $X_1X_2X_3X_4X_5$ which is counted from the third cysteine from N-terminus and reversely counted back to N-terminus, wherein $X_1$ can be an aromatic, hydrophobic or long-chain amino acid, $X_2$ is glutamine, $X_3$ is serine, X4 is alanine and $X_5$ is proline.

Therefore, the invention also provides a therapeutic antagonist, including a peptide which is represented as an amino acid sequence. The amino acid sequence is made via modification of amino acids at the specific position, so that the amino acid sequence carries a modified sequence and the structure of this invention has an extroversion loop structure. The amino acid at the specific region forms a sequence represented as $X_1X_2X_3X_4X_5$, which is counted from the third cysteine of N-terminus and reversely counted back to N-terminus. In a preferred embodiment, $X_1$ is phenylalanine, $X_2$ is glutamine, $X_3$ is serine, X4 is alanine and $X_5$ is proline.

In ELR-$CX_nC$ sequence at N-terminus, in a preferred embodiment, none or at least one the amino acid can be presented between the first cysteine and the second cysteine, such as glutamine, valine, threonine and/or methionine.

This invention provides a therapeutic antagonist for treating diseases induced by cells carrying CXCR1 or CXCR2 receptor activated by ELR-CXC chemokine. The therapeutic antagonist includes an effective amount of at least one ELR-CXC chemokine analog to patients, as well as a pharmaceutically acceptable recipient. The diseases induced by CXCR1 or CXCR2 activated by ELR-CXC chemokine includes acute inflammation induced by neutrophils, chronic inflammation induced by neutrophils, acute inflammatory pain, chronic inflammatory pain, acute neuropathic pain, chronic neuropathic pain, psoriasis, atopic dermatitis, asthma, chronic obstructive pulmonary disease (COPD), pneumonia, pulmonary infiltrates, pleural effusion, adult respiratory disease, arthritis, inflammatory bowel disease, Crohn's disease, ulcerative colitis, septic shock, endotoxic shock, Gram's negative septicemia, toxic shock syndrome, stroke, reperfusion disease in heart and kidney, glomerulonephritis, thrombosis, Alzheimer's disease, graft versus host reaction, homograft rejection, malaria, acute dyspnea syndrome, delayed hypersensitivity, atherosclerosis, ischemia in brain and heart, osteoarthritis, multiple sclerosis, restenosis, angiogenesis, osteoporosis, gingivitis, respiratory virus, herpes virus, hepatitis virus, human immunodeficiency virus (HIV), Kaposi's sarcoma associated with virus, meningitis, cystic fibrosis, birth premature, cough, pruritus, multiple organ dysfunction, trauma, industrial accident, sprain, bruise, psoriatic arthritis, herpes, encephalitis, central nervous system (CNS) obliterans, traumatic brain injury, central nervous system (CNS) tumor, subarachnoid hemorrhage, trauma after surgery, interstitial pneumonia, hypersensitivity, arthrosis induced by crystals, acute and chronic pancreatitis, acute alcoholic hepatitis, necrotizing enterocolitis, chronic sinusitis, ocular neovascular disease, eye inflammation, retinopathy of prematurity, retinopathy of diabetes patient, macular degeneration with the preferred humid and corneal neovascularization, polymyositis, obliterans, acnes, gastric and duodenal ulcer, celiac disease, esophagitis, glossitis, airflow obstruction, high response of airway, bronchiectasis, bronchiolitis, obliterating bronchiolitis, chronic bronchitis, corpulmonale, cough, hard breathing, emphysema, hypercapnia, hyperemphysema, inflammation induced by hypoxemia or hyperoxia, hypoxia, lung volume reduction by surgery, pulmonary fibrotic degeneration, pulmonary hypertension, right ventricular hypertrophy, peritonitis associated with continuous ambulatory peritoneal dialysis (CAPD), granulocytic Ehrlich's disease, sarcoidosis, bronchial disease, ventilation/perfusion mismatching, wheeze, cold, gout, alcoholic hepatitis, lupus, flash burn therapy, periodontitis, graft reperfusion injury and early transplant rejection, acute inflammation, and rheumatic arthritis.

This invention also provides a therapeutic antagonist for using in the treatments of patients on acute inflammatory pain, chronic inflammatory pain, acute neuropathic pain or chronic neuropathic pain, wherein it includes an effective amount of at least one ELR-CXC chemokine analog for administering the patients, as well as a pharmaceutically acceptable excipient.

The invention also provides a therapeutic antagonist for using in the treatments on patients of ocular neovascular disease, such as eye inflammation, retinopathy of prematurity, retinopathy of diabetes patient, macular degeneration with the preferred humid and corneal neovascularization, wherein it includes an effective amount of at least one ELR-CXC chemokine analog for administering the patients, as well as a pharmaceutically acceptable excipient.

This invention also provides a therapeutic antagonist for using in the treatments on patients of gingivitis, respiratory virus, herpes virus, hepatitis virus, HIV, Kaposi's sarcoma associated with virus, and atherosclerosis, wherein it includes an effective amount of at least one ELR-CXC chemokine analog for administering the patients, as well as a pharmaceutically acceptable excipient.

DETAILED DESCRIPTION OF THE INVENTION

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

Figure 2:
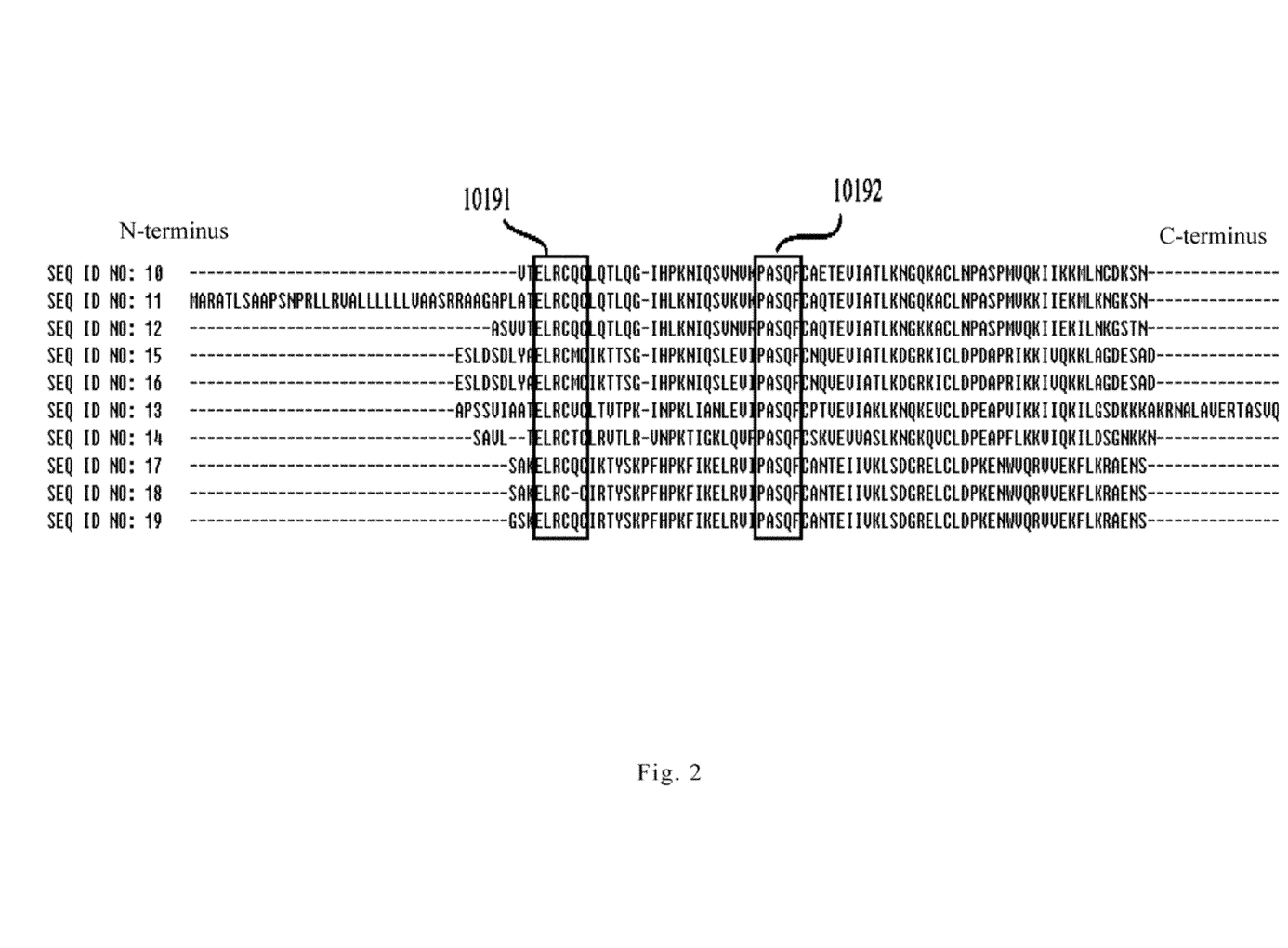
FIG. 2 illustrates the comparison of sequence alignment to the amino acid sequences of the modified chemokine peptides (SEQ ID NO: 10 to SEQ ID NO: 19) in this invention.

This invention provides but not limit in ten ELR-CXC chemokine analogs in the following embodiments. The ELR-CXC chemokine analogs are a modified chemokine peptide, and the denotations of their amino acid sequences respectively are SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18 and SEQ ID NO: 19 (FIG. 2). Here, as shown in FIG. 2, the amino acid sequence of SEQ ID NO: 17 is taken as the illustration. SEQ ID NO: 17 not only has the N-terminus sequence 10191 of ELR-CQC to satisfy the rule of amino acid characteristic sequence of ELR-$CX_nX$, but SEQ ID NO: 17 also has an oligopeptide sequence, Pro-Ala-Ser-Gln-Phe (PASQF, 10192), counted from N-terminus. PASQF is a modified sequence, and is inserted into the upstream of the third cysteine (C) counted from N-terminus, and this third cysteine closely neighbors to phenoalanine (F) of PASQF oligopeptide sequence.

It could be known from the sequences provided in this invention that the sequences, SEQ ID NO: 10 to SEQ ID: 19, of ELR-CXC chemokine analogs all have a PASQF modified sequence which is counted from the third cysteine of N-terminus.

Figure 1:
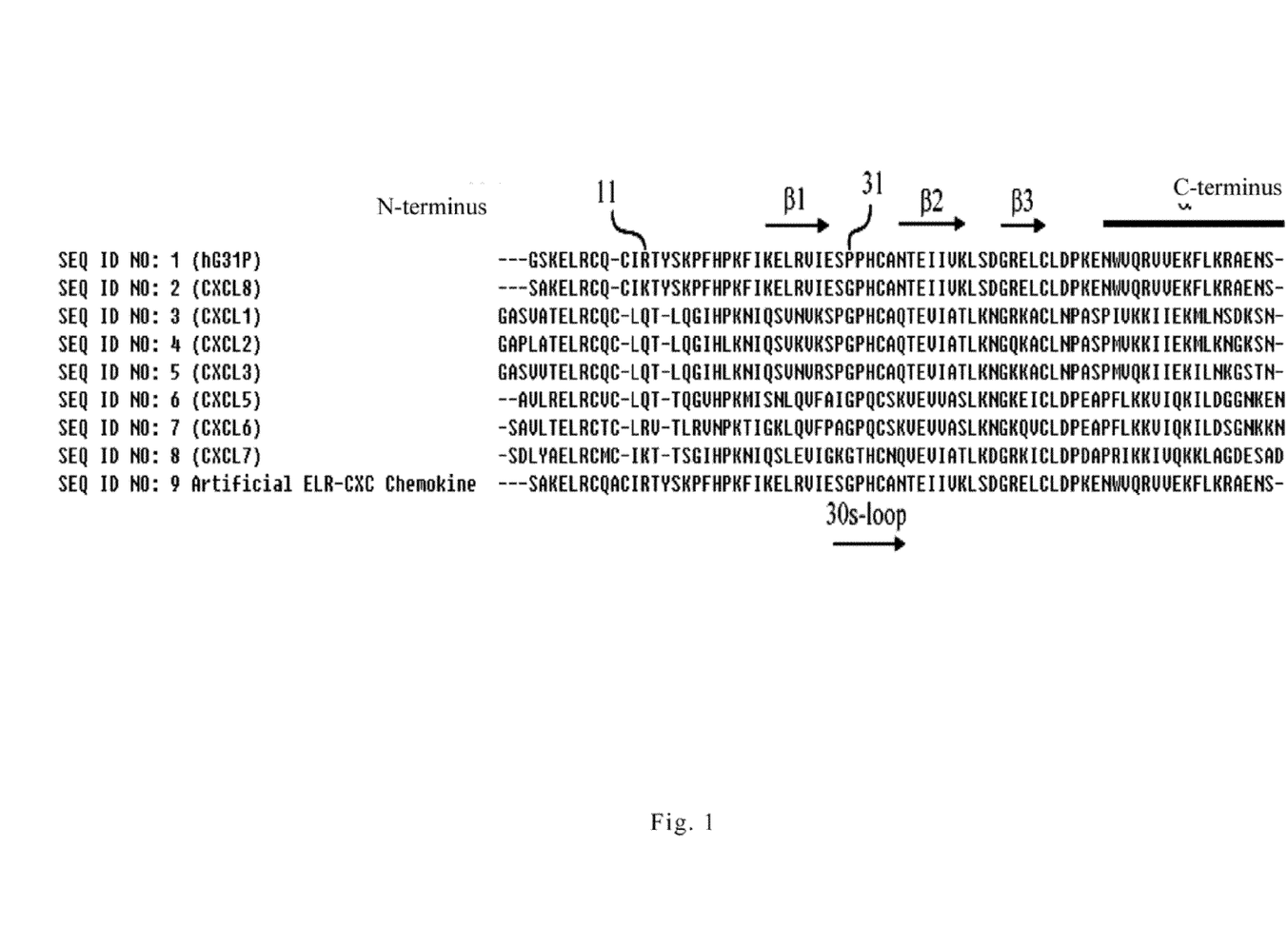
FIG. 1 illustrates the comparison of sequence alignment to the source chemokine peptide sequences (SEQ ID NO:1 to SEQ ID NO: 9), i.e. the amino acid sequences of ELR-CXC chemokines with high affinity to CXCR1 or/and CXCR2.

The source chemokine peptide related to this invention is shown as FIG. 1, which is the amino acid sequence alignment of ELR-CXC chemokines, wherein CXCL1 (SEQ ID NO: 3), CXCL2 (SEQ ID NO: 4), CXCL3 (SEQ ID NO: 5), CXCL5 (SEQ ID NO: 6), CXCL6 (SEQ ID NO: 7), CXCL7 (SEQ ID NO: 8), CXCL8 (SEQ ID NO: 2), hG31P (SEQ ID NO: 1) and artificial ELR-CXC chemokine (SEQ ID NO: 9) belong to ELR-CXC chemokines or the examples of the receptors having high affinity on CXCR1 or CXCR2. Modification is made in accordance with this type of chemokine in this invention, and it mainly depends on inserting a PASQF characteristic sequence into the 30s-loop region (FIG. 1). This PASQF originally exists in CXCL10 chemokine, which is a non-ELR-CXC chemokine.

Figure 3:
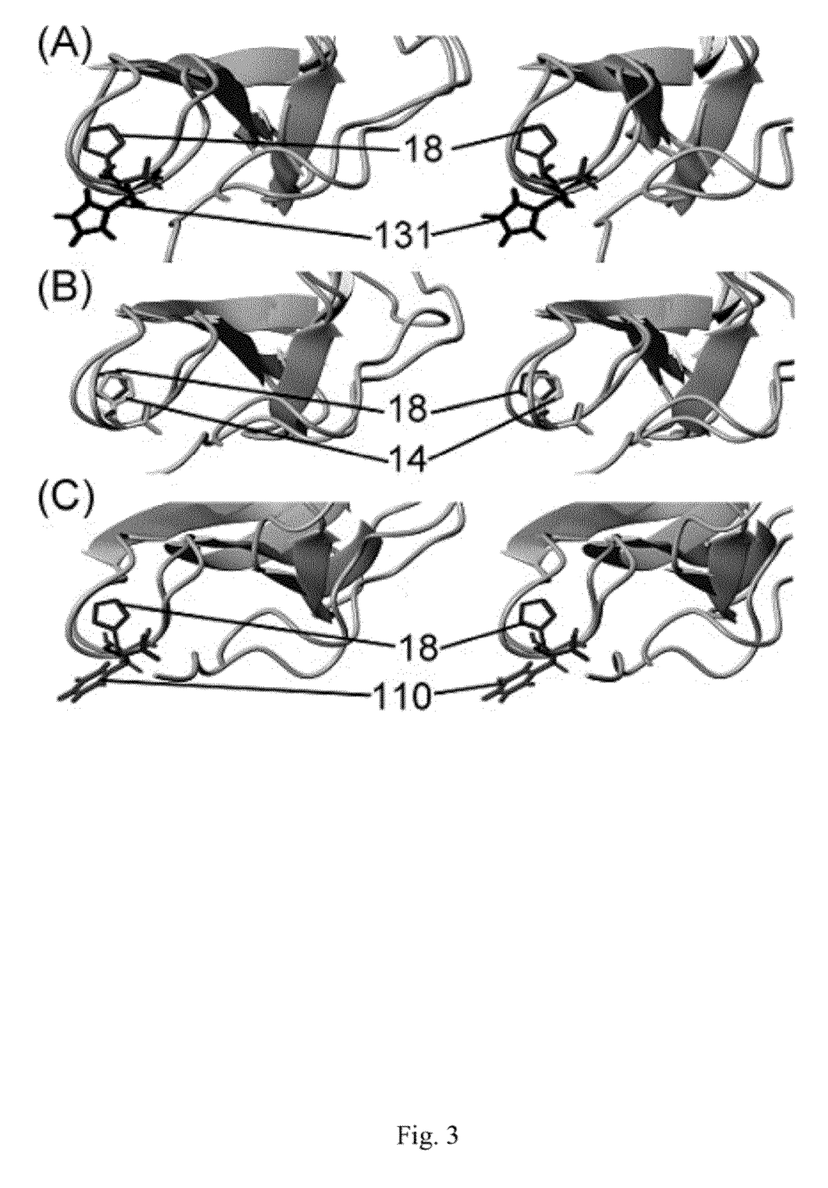
FIG. 3(A) to FIG. 3(C) illustrate the comparisons on loop structures of CXCL4, CXCL8, CXCL10 and hG31P.

Among this, SEQ ID NO: 2 (CXCL8) is the original sequence mainly corresponding to CXCR1 or CXCR2 receptor among ELR-CXC chemokines, and the embedded loop structure 18 can be seen in FIG. 3(A), 3(B) or 3(C). Although CXCL4 in FIG. 3(B) also has an embedded loop structure 14 and its stereo structure is similar to that of CXCL8 (referring to 18, 14 of FIG. 3(B)), it still can be differentiated from CXCL8 in functions due to its N-terminus belonging to non-ELR-CXC. hG31P is a sequence having double mutations, the 11th amino acid is modified from lysine (K) to arginine (R) (11), and the 31th amino acid is modified from glycine (G) to proline (P) (31). Its stereostructure is shown in 131 of FIG. 3(A), so that the protein structure of the chemokine has a structure similar to the extroversional loop structure 131 of CXCL10 in FIG. 3(C). CXCL10 is a chemokine which has a PASQF sequence at the upstream of the third cysteine from N-terminus, but it does not has the characteristic of ELR-CXC chemokine at N-terminus. FIG. 3(C) is that the protein structure of CXCL10 is an extroversional loop structure 110 after folding. It is similar to the extroversioanl loop structure 131 of hG31P in FIG. 3(A), but it shows the difference on spin angle. If SEQ ID NO: 17 of FIG. 2 is taken as the example in this invention, in addition to that N-terminus has ELR-CXC characteristic in accordance with the backbones of SEQ ID NO: 1 to SEQ ID NO: 9, modification is further made at the 30s-loop sequence between β1 sheet and β2 sheet to add PASQF sequence in SEQ ID NO: 17, so that SEQ ID NO: 17 has the extroversional loop structure 110 similar to CXCL10, to be the example of loop structure in the embodiment of SEQ ID NO: 17 in this invention.

It can be known from FIG. 1 that the similarity of those sequences is relatively high, especially on the α-helix and β-sheet structures, such as β1, β2 and β3 sequence region and α sequence region. However, it is observed that residues, glycine G31 and proline P32, are highly conservative in ELR-CXC. The major modification region in this invention is thus 30s-loop region.

Figure 4:
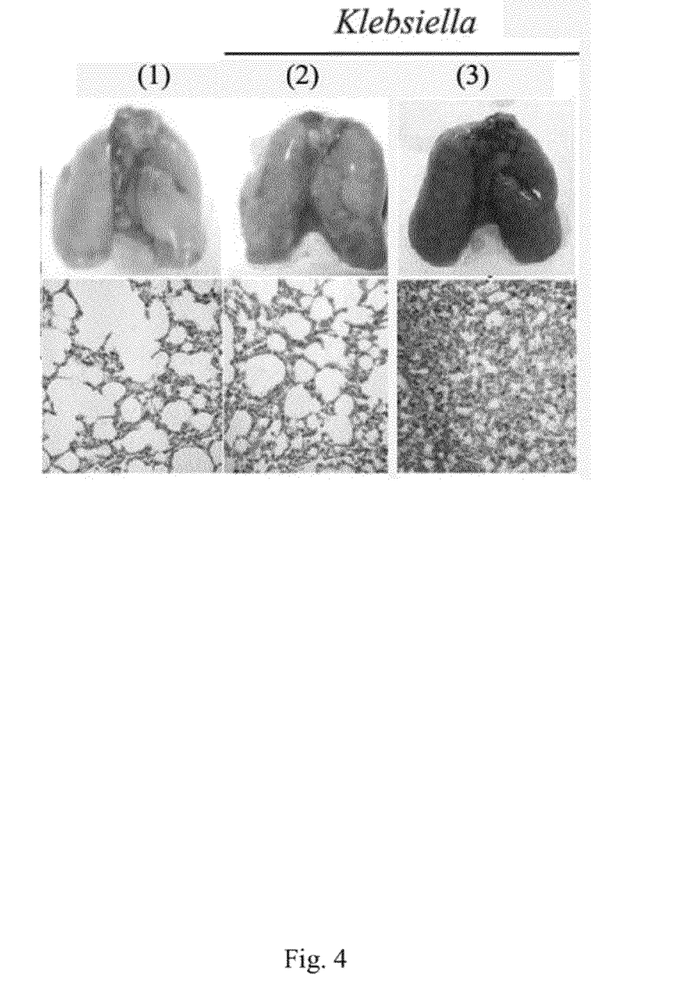
FIG. 4 illustrates the treatment effects of ELR-CXC chemokine therapeutic antagonist of this invention on guinea pig's pneumonia induced by *Klebsiella*: (1) normal lung tissue; (2) lung tissue infected with *Klebsiella* and treated with receptor protein of this invention; and (3) lung tissue infected with *Klebsiella*.

FIG. 4 shows the lung specimen and the lung tissue section specimen. After treating pneumonia in guinea pigs with ELR-CXC therapeutic antagonist of the embodiment in this invention, the lung tissue with pneumonia is reversed to the normal lung tissue, as observed in the section specimens, indicating that ELR-CXC therapeutic antagonist in this invention can be used to cure pneumonia.

Figure 5:
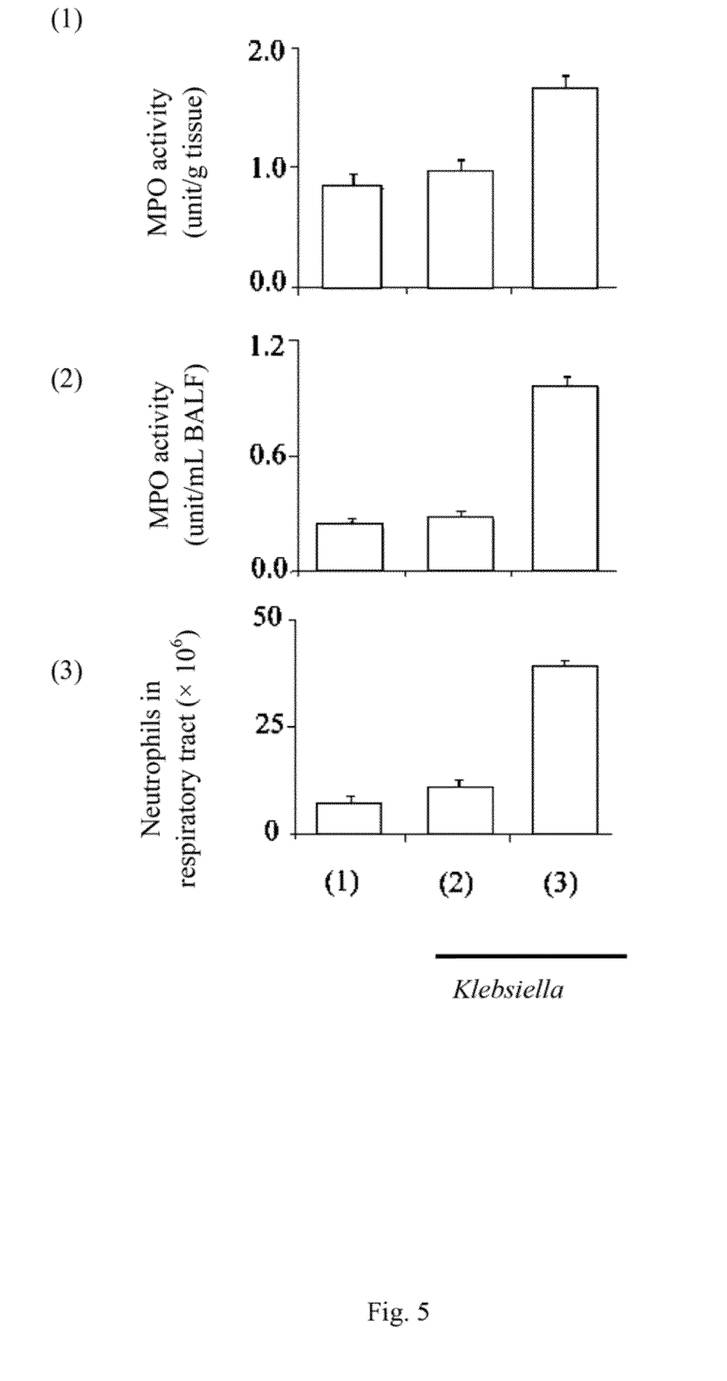
FIG. 5 illustrates the treatment effects of ELR-CXC chemokine therapeutic antagonist of this invention on guinea pig's pneumonia induced by *Klebsiella*: (1) myeloperoxidase (MPO) activity in the tissue; (2) MPO activity in the bronchoalveolar lavage fluid (BALF); (3) the amount of neutrophils in the airway. Numbers 1, 2 and 3 in horizontal axis respectively are referred to the normal lung tissue, the lung tissue infected with *Klebsiella* and treated with receptor protein of this invention; and the lung tissue infected with *Klebsiella*.

FIG. 5 indicates that, after treating pneumonia in guinea pigs with ELR-CXC chemokine therapeutic antagonist, the activities of myeloperixidase (MPO) in both lung tissue and in the bronchoalveolar lavage fluid (BALF), as well as the numbers of neutrophils in respiratory tract are reversed to the same level in normal guinea pigs. It can be known from FIG. 3 and FIG. 4 that the ELR-CXC therapeutic antagonist of this invention can be applied to treat diseases involved in immune, inflammation and so on.

Figure 6:
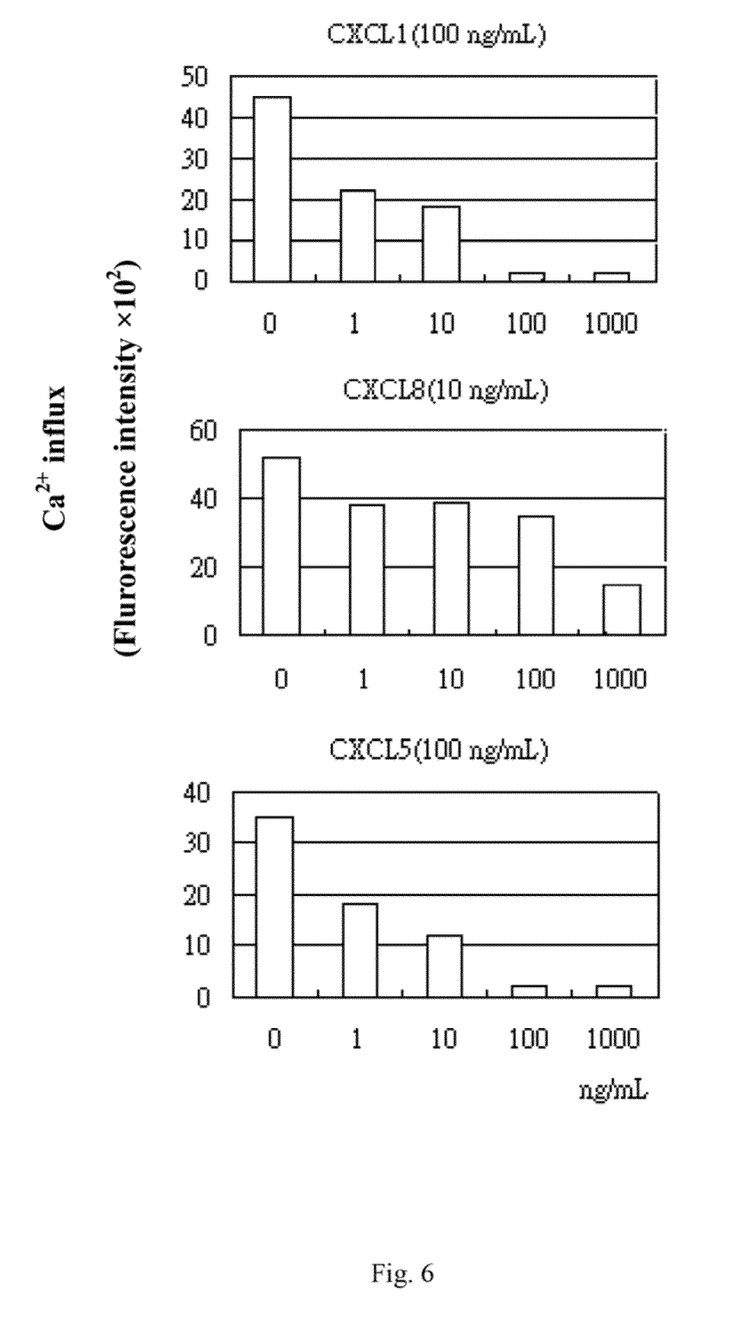
FIG. 6 illustrates inhibition effects of different concentrations of ELR-CXC chemokine on calcium signal induced by neutrophils: (1) activity induced by antagonizing CXCL1; (2) activity induced by antagonizing CXCL8; and (3) activity induced by antagonizing CXCR5. Horizontal axis is referred to the inhibitory effects of different concentration of ELR-CXC, and Vertical axis is referred to the intensity of intracellular calcium signal measured by Flou-3-AM.

As shown in FIG. 6, it indicates that the different dosages of ELR-CXC chemokine therapeutic antagonist of this invention show the inhibition effect of intracellular calcium ion signal intensity induced by ELR-CXC chemokines such as CXCL1, CXCL5 and CXCL8.

Figure 7:
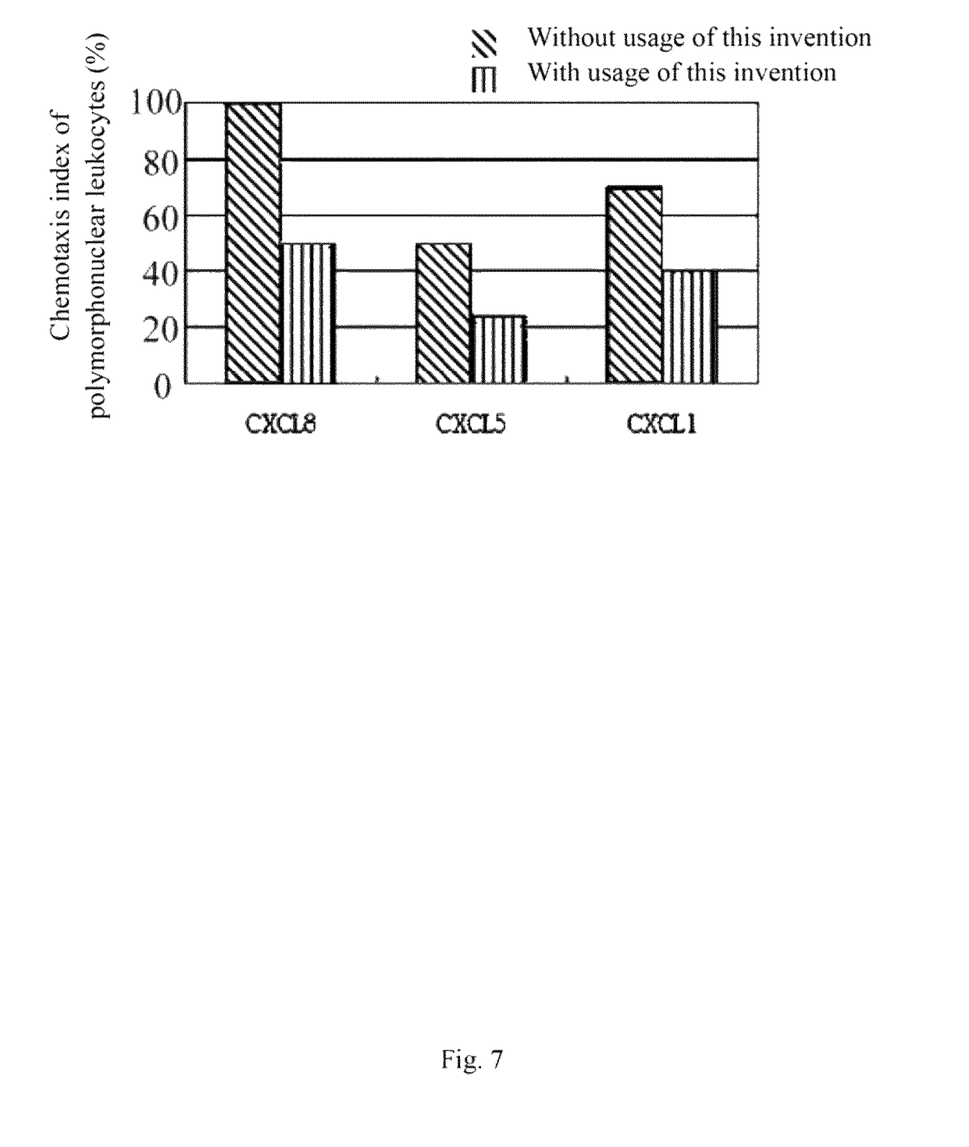
FIG. 7 illustrates inhibition effects of different concentrations of ELR-CXC chemokine on chemotaxis induced by neutrophiles. The concentrations of ELR-CXC chemokines, CXCL8, CXCL5 and CXCL1, are 10, 100 and 100 ng/mL, respectively. Horizontal axis is chemotaxis difference generated by different ELR-CXC chemokines with or without ELR-CXC chemokine antagonist of this invention. Slash bar is referred to the effect for ELR-CXC chemokine alone without ELR-CXC antagonist of this invention, and straight line bar is referred to the effect generated after the addition of ELR-CXC chemokine therapeutic antagonist of this invention.

As shown in FIG. 7, it indicates that the addition of ELR-CXC chemokine therapeutic antagonist of this invention can inhibit the effect of chemotaxis generated by neutrophils.

In conclusion, this invention is the therapeutic antagonist for CXCR1 or/and CXCR2 receptor, capable of suppressing the abnormal signal transmission induced by those two receptors through ELR-CXC activation. Therefore, therapy can be made on various related diseases caused by cells carrying this abnormal signal transmission, such as acute inflammation (e.g. symptoms such as pulmonary infiltrates, pleural effusion and so on induced by pneumonia) or chronic inflammation (e.g. diseases such as rheumatoid arthritis, chronic obstructive pulmonary disease and so on) induced by CXCR1 or/and CXCR2-expressing neutrophils among leukocytes through ELR-CXC activation. Alternatively, for instance, the caused related diseases include angiogenesis accompanied by tumor growth inhibition.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A modified chemokine peptide which is used as an antagonistic peptide for a chemokine receptor, including an amino acid sequence having an N-terminus, the amino acid sequence comprising:
   a glutamate (E)-leucine (L)-arginine (R) characteristic sequence situated at the N-terminus of the chemokine peptide; and
   a modified sequence situated at a region represented as $X_5X_4X_3X_2X_1$-$Cys^3$ from N-terminus to C-terminus, wherein the $Cys^3$ is a third cysteine ($Cys^3$) from the N-terminus,
   wherein $X_1$ is an aromatic amino acid, an hydrophobic amino acid or a long-chain amino acid, $X_2$ is glutamine (Q), $X_3$ is serine (S), $X_4$ is alanine (A), $X_5$ is proline (P), and the length of the modified chemokine peptide is 70-107 amino acids.

2. The modified chemokine peptide according to claim 1, wherein the aromatic amino acid includes tryptophan (W), phenylalanine (F) or tyrosine (Y).

3. The modified chemokine peptide according to claim 2, wherein the aromatic amino acid is phenylalanine (F).

4. The modified chemokine peptide according to claim 1, wherein an un-modified precursor of the modified chemokine peptide is originated from a source chemokine peptide, null to two amino acids exist between a first cysteine (C) and a second cysteine (C) of an N-terminus of the source chemokine peptide, and the amino acid is a polar amino acid with charge or without charge when the number of the amino acid is one to two.

5. The modified chemokine peptide according to claim 4, wherein the source chemokine peptide is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and the combination thereof.

6. The modified chemokine peptide according to claim 1, wherein the amino acid sequence is selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and the combination thereof.

7. The modified chemokine peptide according to claim 1, wherein the chemokine receptor is CXCR1 or CXCR2.

8. A pharmaceutical composition, comprising a modified chemokine peptide of claim 1 and a pharmaceutically acceptable recipient.

9. The pharmaceutical composition according to claim 8, wherein the modified chemokine peptide is used to treat a disease resulted from abnormal signal transmissions induced by CXCR1 or CXCR2 activation.

10. The pharmaceutical composition according to claim 9, wherein the disease is selected from the group consisting of acute inflammation induced by neutrophils, chronic inflammation induced by neutrophils, acute inflammatory pain, chronic inflammatory pain, acute neuropathic pain, chronic neuropathic pain, psoriasis, atopic dermatitis, asthma, chronic obstructive pulmonary disease (COPD), pneumonia, pulmonary infiltrates, pleural effusion, adult respiratory disease, arthritis, inflammatory bowel disease, Crohn's disease, ulcerative colitis, septic shock, endotoxic shock, Gram's negative septicemia, toxic shock syndrome, stroke, reperfusion disease in heart or kidney, glomerulonephritis, thrombosis, Alzheimer's disease, graft versus host reaction, homograft rejection, malaria, acute dyspnea syndrome, delayed hypersensitivity, atherosclerosis, ischemia in brain or heart, osteoarthritis, multiple sclerosis, restenosis, angiogenesis, osteoporosis, gingivitis, respiratory virus, herpes virus, hepatitis virus, human immunodeficiency virus (HIV), Kaposi's sarcoma associated with virus, meningitis, cystic fibrosis, premature birth, cough, pruritus, multiple organ dysfunction, trauma, sprain, bruise, psoriatic arthritis, herpes, encephalitis, central nervous system (CNS) obliterans, traumatic brain injury, central nervous system (CNS) tumor, subarachnoid hemorrhage, trauma after surgery, interstitial pneumonia, hypersensitivity, arthritis induced by crystals, acute and chronic pancreatitis, acute alcoholic hepatitis, necrotizing enterocolitis, chronic sinusitis, ocular neovascular disease, eye inflammation, retinopathy of prematurity, retinopathy of diabetes patient, polymyositis, obliterans, acne, gastric or duodenal ulcer, celiac disease, esophagitis, glossitis, airflow obstruction, bronchiectasis, bronchiolitis, obliterating bronchiolitis, chronic bronchitis, corpulmonale, cough, hard breathing, emphysema, hypercapnia, hyperemphysema, inflammation induced by hypoxemia or hyperoxia, hypoxia, pulmonary fibrotic degeneration, pulmonary hypertension, right ventricular hypertrophy, peritonitis associated with continuous ambulatory peritoneal dialysis (CAPD), granulocytic Ehrlich's disease, sarcoidosis, bronchial disease, wheeze, cold, gout, alcoholic hepatitis, lupus, periodontitis, graft reperfusion injury and early transplant rejection, acute inflammation, and rheumatic arthritis.

11. The pharmaceutical composition according to claim 10, wherein the disease is selected from the group consisting of acute inflammation induced by neutrophils, chronic inflammation induced by neutrophils, chronic obstructive pulmonary disease (COPD), pneumonia, pulmonary infiltrates, pleural effusion, rheumatoid arthritis, acute inflammatory pain, chronic inflammatory pain, acute inflammation, and chronic inflammation.

* * * * *